(12) United States Patent
Komatsu et al.

(10) Patent No.: US 10,550,277 B2
(45) Date of Patent: Feb. 4, 2020

(54) INK COMPOSITION, INK SET, AND RECORDING METHOD

(71) Applicant: Seiko Epson Corporation, Tokyo (JP)

(72) Inventors: Hidehiko Komatsu, Chino (JP); Yasuhiro Oki, Matsumoto (JP); Daisuke Sakuma, Minowa (JP); Hiroyuki Kaneko, Minowa (JP); Yuki Wakushima, Matsumoto (JP)

(73) Assignee: Seiko Epson Corporation (JP)

( * ) Notice: Subject to any disclaimer, the term of this patent is extended or adjusted under 35 U.S.C. 154(b) by 289 days.

(21) Appl. No.: 15/632,811

(22) Filed: Jun. 26, 2017

(65) Prior Publication Data

US 2017/0369721 A1 Dec. 28, 2017

(30) Foreign Application Priority Data

Jun. 27, 2016 (JP) .................................. 2016-126472
May 30, 2017 (JP) .................................. 2017-106597

(51) Int. Cl.
*C09D 11/328* (2014.01)
*C09D 11/40* (2014.01)
(Continued)

(52) U.S. Cl.
CPC ............... *C09D 11/107* (2013.01); *B41J 2/01* (2013.01); *C07D 253/02* (2013.01);
(Continued)

(58) Field of Classification Search
None
See application file for complete search history.

(56) References Cited

U.S. PATENT DOCUMENTS 5,750,662 A * 5/1998 Reichert ............. C09B 62/4415
534/612
6,051,036 A 4/2000 Kusaki et al.
(Continued)

FOREIGN PATENT DOCUMENTS

JP 05-272077 A 10/1993
JP 06-057654 A 3/1994
(Continued)

OTHER PUBLICATIONS

Extended European Search Report for Application No. EP 18 17 4965 dated Sep. 18, 2018 (7 pages).

*Primary Examiner* — Helene Klemanski
(74) *Attorney, Agent, or Firm* — Harness, Dickey & Pierce, P.L.C.

(57) ABSTRACT

An ink composition contains a first dye represented by formula (I)

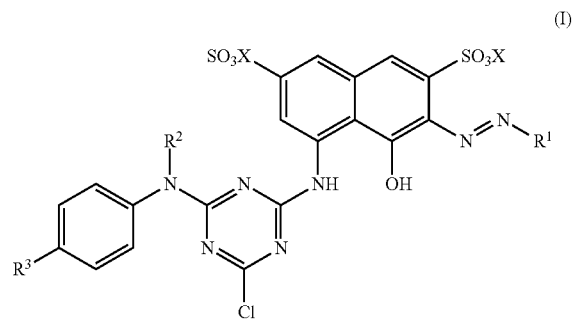

and a second dye represented by formula (II)
(Continued)

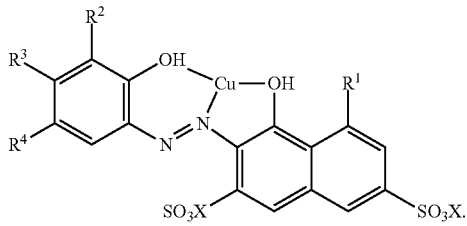

(II)

16 Claims, 2 Drawing Sheets

(51) Int. Cl.
*B41J 2/01* (2006.01)
*C07D 251/22* (2006.01)
*C09D 11/107* (2014.01)
*C09D 11/322* (2014.01)
*C09D 11/023* (2014.01)
*C07D 253/02* (2006.01)

(52) U.S. Cl.
CPC .......... *C09D 11/023* (2013.01); *C09D 11/322* (2013.01); *C09D 11/40* (2013.01)

(56) References Cited

U.S. PATENT DOCUMENTS

| | | | |
|---|---|---|---|
| 6,331,052 B1 * | 12/2001 | Murai | B41J 2/04581 347/10 |
| 6,352,563 B1 | 3/2002 | Kusaki et al. | |
| 6,379,442 B1 * | 4/2002 | Lavery | C09D 11/328 106/31.48 |
| 6,521,032 B1 * | 2/2003 | Lehmann | C09D 11/328 106/31.51 |
| 6,843,838 B2 * | 1/2005 | Zimmer | C09D 11/40 106/31.27 |
| 9,533,505 B2 * | 1/2017 | Watanabe | B41J 2/1606 |
| 9,909,024 B2 * | 3/2018 | Komatsu | C09D 11/328 |
| 10,259,961 B2 * | 4/2019 | Oki | C09B 62/09 |
| 2004/0068103 A1 * | 4/2004 | Baettig | C09D 11/328 534/674 |
| 2004/0187736 A1 | 9/2004 | Taguchi et al. | |
| 2005/0160937 A1 * | 7/2005 | Gremaud | C09D 11/40 106/31.48 |
| 2005/0211134 A1 | 9/2005 | Gremaud et al. | |
| 2005/0243129 A1 * | 11/2005 | Kim | B41J 2/14129 347/45 |
| 2007/0097162 A1 * | 5/2007 | Iwashita | B41J 2/06 347/9 |
| 2008/0068412 A1 * | 3/2008 | Kikuchi | B41J 2/2132 347/12 |
| 2015/0000051 A1 | 1/2015 | Tzikas et al. | |

FOREIGN PATENT DOCUMENTS

| | | |
|---|---|---|
| JP | 2000-265099 A | 9/2000 |
| JP | 2003-012976 A | 1/2003 |
| JP | 2004-307832 A | 11/2004 |
| JP | 2012-241075 A | 12/2012 |

* cited by examiner

INK COMPOSITION, INK SET, AND RECORDING METHOD

BACKGROUND

1. Technical Field

The present invention relates to an ink composition, an ink set, and a recording method.

2. Related Art

Ink jet recording is a recording method in which ink droplets are ejected from fine nozzles and attaching them to a recording medium, producing images. The system used is relatively affordable, and the images are recorded quickly with high resolution and high quality. Because of numerous considerations involved, such as the characteristics of the inks used, the stability of the recording process, and the quality of the resulting images, the current active research on ink jet recording does not only focus on recording devices but also includes ink compositions used.

For example, there have been studies on how to improve the light fastness and stability over time of images printed (recorded) using ink compositions for ink jetting. In the technology described in JP-A-2004-307832, dark yellow ink is mixed with yellow, magenta, and cyan dyes to improve the stability of images over time.

Ink jet recording has also been used to dye fabric or similar materials (textile printing or applying color to fabric). As an alternative to the conventional methods for dyeing fabric (woven and nonwoven fabrics) such as screen printing and roller printing, various ink jet recording methods have been studied because of the advantages they provide, such as high productivity in high-mix low-volume manufacturing and quickness in printing. For example, JP-A-6-057654 discloses using a set of yellow (Y), magenta (M), cyan (C), and black (K) ink compositions in combination with a violet (V) ink composition to extend the color gamut of the resulting images.

Ink compositions for textile printing contain, for example, a dye as a colorant, and a great variety of dyes are available. However, the options may be limited when selecting dyes for a particular purpose, such as ones suitable for the fabric, ones compatible with the base liquid (oil, water, etc.) of the ink composition, and ones that give the desired color. In the dyeing of cotton and silk fabrics, for example, C.I. Reactive Red 31 is one of dyes capable of coloring both types of fabrics and selected as being suitable for use as an aqueous ink composition.

Research by the inventors, however, has revealed that C.I. Reactive Red 31, when used in an aqueous ink for textile printing, causes a decrease in the pH of the ink over time. With such an ink, which experienced a change in pH over time, it can be difficult to color the fabric as designed because of differences in hue between the areas dyed with the altered ink and the areas dyed with intact ink. Another finding from the inventors' research is that dyeing different production lots of polyamide fabrics, such as silk and wool, with such an ink quite often results in the fabric being dyed in different hues; such an ink has an insufficient "range of compatibility with fabrics," a measure of how little hue variation an ink produces when used to dye different kinds of fabrics or different lots of a fabric between which the characteristics of fiber are dissimilar.

When using a combination of multiple dyes to extend the color gamut, furthermore, it is difficult to obtain an ink composition satisfactory in all of the characteristics of hue, pH stability, light fastness, and color gamut simply by mixing dyes in different colors with no care about compatibility between the dyes.

SUMMARY

An advantage of some aspects of the invention is that an ink composition is provided that is stable over time in terms of pH, superior in color strength, range of compatibility with fabrics, and light fastness when used in textile printing, and gives ink sets made therewith a wide color gamut. Another advantage is that an ink set and a recording method with a wide color gamut are provided.

The following describes some aspects or exemplary applications of the invention.

An aspect of the invention is an ink composition. This ink composition contains at least one first dye represented by formula (I)

[Chem. 1]

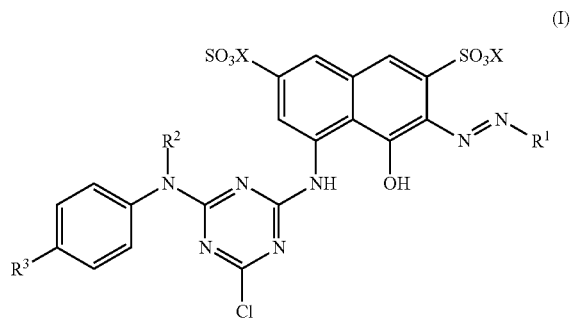

(I)

(where $R^1$ denotes

[Chem. 2]

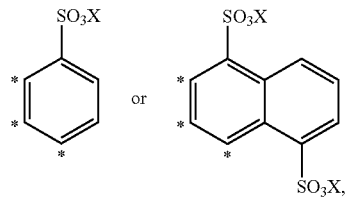

or
$R^2$ denotes H, $CH_3$, or $C_2H_5$, and
$R^3$ denotes H or

[Chem. 3]

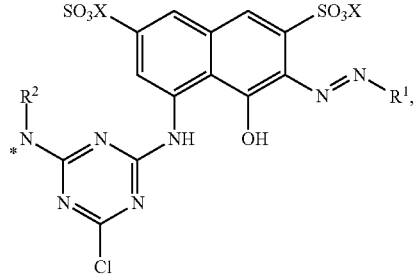

where X denotes H, Li, Na, or K,
with possible binding sites labeled with an asterisk) and at least one second dye represented by formula (II)

[Chem. 4]

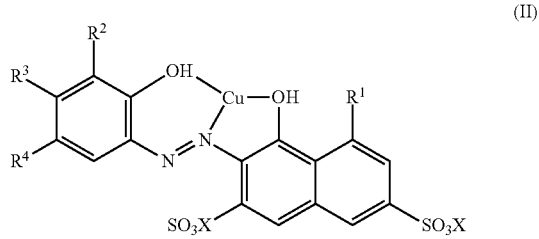

(II)

(where $R^1$ denotes $SO_3X$ or

[Chem. 5]

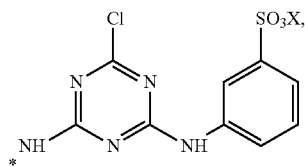

$R^2$, $R^3$, and $R^4$ each independently denote H, $SO_3X$, a halogen, or

[Chem. 6]

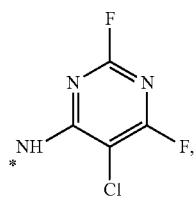

and
X denotes H, Li, Na, or K,
with possible binding sites labeled with an asterisk).

Such an ink composition is stable over time in terms of pH by virtue of the appropriate chemical structure of the first and second dyes, and, when used in textile printing, gives prints high color strength. The ink composition has a wide range of compatibility with fabrics too, allowing the user to dye different production lots of fabric with little variation in hue, whether the fabric is a cellulose fabric, such as cotton or viscose, or a polyamide fabric, such as silk or wool. The chemical structure of the first and second dyes is highly resistant to light and will give high light fastness to prints made using the ink composition. When used as a component of an ink set, furthermore, the ink composition allows the user to perform textile printing with a wide color gamut.

In an embodiment of the invention, the ink composition may have a pH of 6.0 or more and 8.5 or less.

This allows the user to dye fabric with higher fidelity to the designed color. With a pH in this range, the ink composition is more stable in terms of the hue it develops on prints made therewith. Ink compositions with a pH in this range, furthermore, can be used with an ink jet recording device causing acceptably limited damage to the device, such as corrosion of a recording head.

In an embodiment of the invention, the ink composition may further contain a pH-adjusting agent.

This makes the ink composition more stable and better in maintaining its pH in the desired range, even when left under conditions under which its pH is likely to change, such as a long period of storage. Such an ink composition is stable in terms of the hue it develops on prints made therewith, helping the user dye fabric with high fidelity to the designed color. By virtue of the pH stability higher than without a pH-adjusting agent, furthermore, such an ink composition can be used with an ink jet recording device only causing acceptably limited damage to the device, such as corrosion of a recording head.

In an embodiment of the invention, the ink composition may contain no or up to 5% by mass, of the total amount of the ink, polyhydric alcohols with boiling points higher than 260° C.

Such an ink composition allows the user to color fabric darker than usual by virtue of the small number of alcoholic hydroxyl groups, a cause of incomplete fixation of dyes in the process of dyeing. This can be described in more detail as follows. The driving force of the fixation of a dye is a reaction between the reactive groups of the dye and hydroxyl groups that vegetable fiber, for example, has. Any alcoholic hydroxyl group can also react with the reactive groups of the dye as with the hydroxyl groups that vegetable fiber, for example, has. If abundant in the ink composition, therefore, alcoholic hydroxyl groups can inhibit the fixation of the dye. However, even if a polyhydric alcohol, an alcohol having two or more hydroxyl groups, is contained in the ink composition, the polyhydric alcohol evaporates quickly, leaving little after the ink composition is applied to the fabric, as long as its boiling point is 260° C. or less. As a result, the number of alcoholic hydroxyl groups left in the ink composition applied to the fabric is small, and it is unlikely that the reaction between the reactive groups of the dye and the hydroxyl groups that vegetable fiber, for example, has is inhibited. The dye is fixed in a stable manner, allowing the user to color the fabric with limited occurrence of faults such as uneven dyeing.

In an embodiment of the invention, the at least one first dye in the ink composition may be selected from C.I. Reactive Red 141, C.I. Reactive Red 24:1, and C.I. Reactive Red 245, and the at least one second dye may be selected from C.I. Reactive Violet 1 and C.I. Reactive Violet 33.

This makes the ink composition more stable in terms of the hue it develops on prints made therewith by virtue of the chemical structure of the first and second dyes that improves the pH stability of the ink composition over time. The ink composition has a wider range of compatibility with fabrics too, allowing the user to dye different production lots of fabric with smaller variation in hue, whether the fabric is a cellulose fabric, such as cotton or viscose, or a polyamide fabric, such as silk or wool. Using at least one in each of the two series of dyes in combination will also lead to an extended color gamut in textile printing and better light fastness.

Another aspect of the invention is an ink set. This ink set includes an above-described ink composition as a first ink composition, along with a yellow ink composition containing C.I. Reactive Yellow 95 or C.I. Reactive Yellow 2, a cyan ink composition containing C.I. Reactive Blue 72 or C.I. Reactive Blue 15:1, and a black ink composition containing C.I. Reactive Black 39.

Such an ink set allows the user to dye different production lots of fabric with little variation in hue, whether the fabric is a cellulose fabric, such as cotton or viscose, or a polyamide fabric, such as silk or wool, and, furthermore, enables textile printing with an extended color gamut. With such an ink set, therefore, the user can produce recordings (prints) with a wide range of compatibility with fabrics.

Another aspect of the invention is a recording method. This recording method includes ejecting an above-described ink composition or the first ink composition in an above-described ink set from an ink jet recording head. The recording head has a nozzle plate that contains fluorine in at least part of the surface thereof and has siloxane bonds less than 1 µm beneath the surface thereof.

In such a recording method, the fluorine, present in at least part of the surface of the nozzle plate of the ink jet recording head, and the siloxane bonds, existing less than 1 µm beneath the surface of the nozzle plate, help the nozzle plate repel the ink composition, effectively protecting the recording head from corrosion by the ink compositions for a long period of time. The surface of the nozzle plate is kept liquid-repellent, allowing the user to eject the ink composition from the ink jet recording head in a stable manner. Preferably, the pH of the ink composition is between 6.5 and 8.5. This ensures the recording head ejects the ink compositions in a stable manner even after the recording head is left unused for a long period of time.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
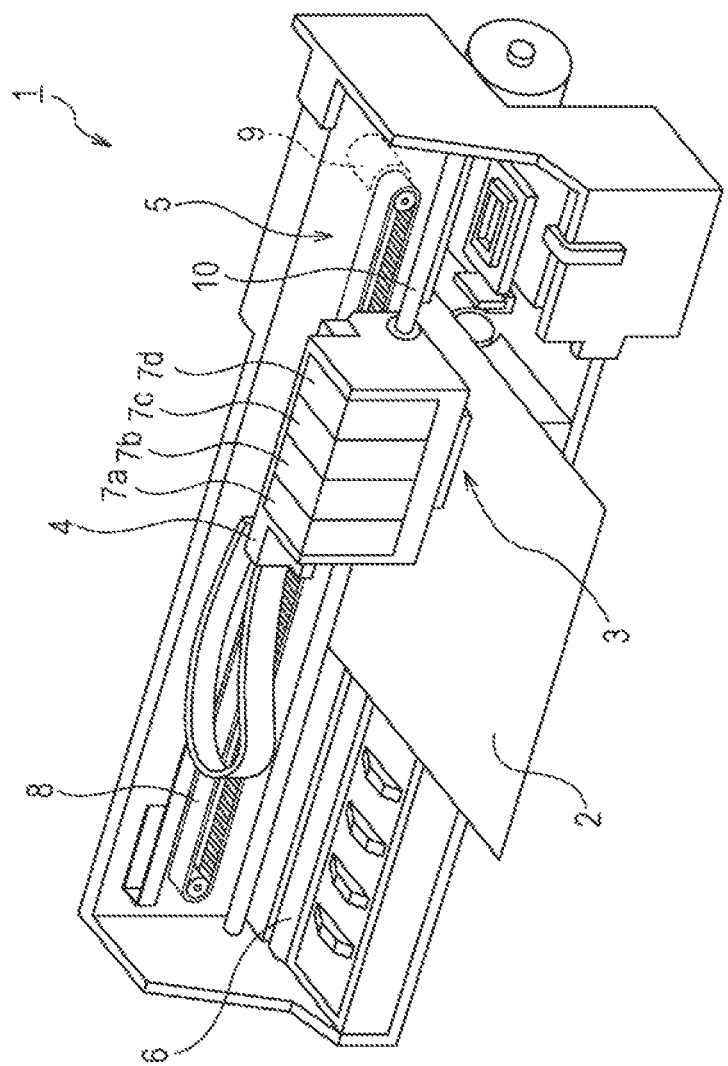
FIG. 1 is a schematic perspective view of an ink jet recording device according to an embodiment.

The following describes some embodiments of the invention. These embodiments are only for illustrative purposes and not meant to limit any aspect of the invention. The invention includes all variations that can be implemented within the scope of the invention. Some of the features described below may be optional.

1. Ink Composition

An ink composition according to this embodiment contains a certain first dye and a certain second dye and is used for textile printing, a process of printing in which the ink composition is applied to fabric by ink jetting.

1.1. First Dye

The first dye in the ink composition according to this embodiment is represented by formula (I):

[Chem. 7]

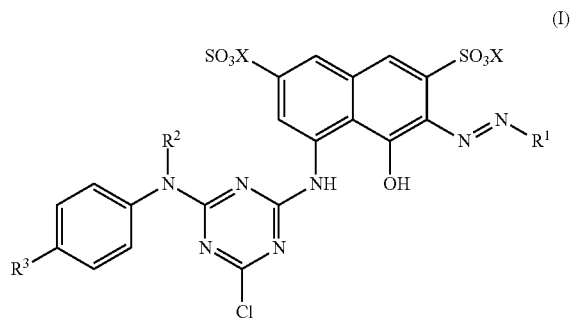

(I)

(where $R^1$ denotes

[Chem. 8]

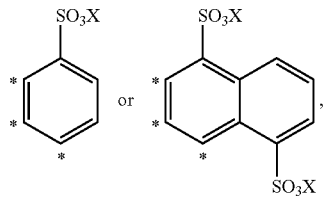

$R^2$ denotes H, $CH_3$, or $C_2H_5$, and $R^3$ denotes H or

[Chem. 9]

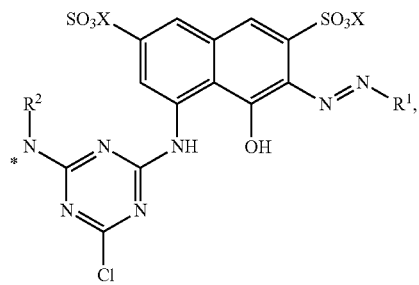

where X denotes H, Li, Na, or K, with possible binding sites labeled with an asterisk).

The first dye is therefore one of the several dyes available as C.I. Reactive Red ##. It should be noted that abbreviated names of dyes may be used herein, such as "RR24" and "RV1" for "C.I. Reactive Red 24" and "C.I. Reactive Violet 1," respectively. The acronym "C.I." stands for Color Index.

Specific examples of first dyes include C.I. Reactive Red 24 (Chemical Abstracts Service Registry Number (CAS): 70210-20-7 or 12238-00-5), represented by the formula below,

[Chem. 10]

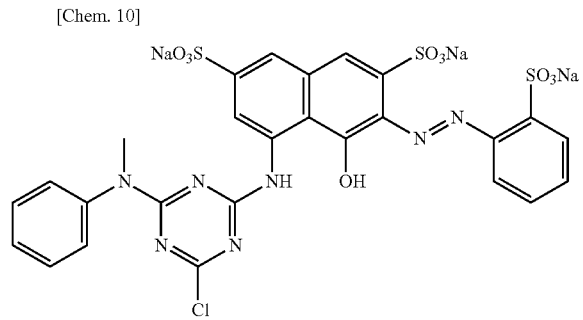

C.I. Reactive Red 24:1 (CAS: 72829-25-5), represented by the formula below,

[Chem. 11]

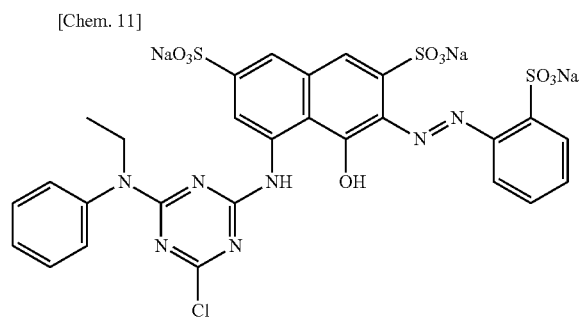

C.I. Reactive Red 141 (CAS: 61931-52-0), represented by the formula below, and

[Chem. 12]

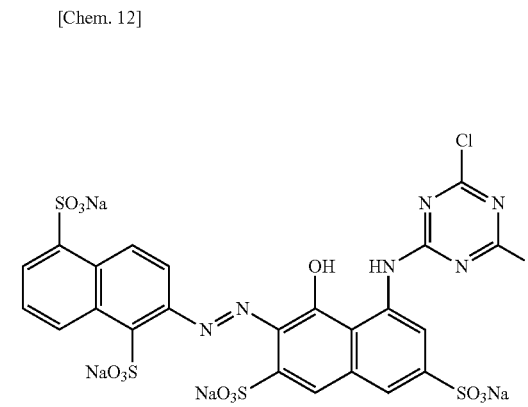

C.I. Reactive Red 245 (CAS: 130210-57-9), represented by the formula below.

[Chem. 13]

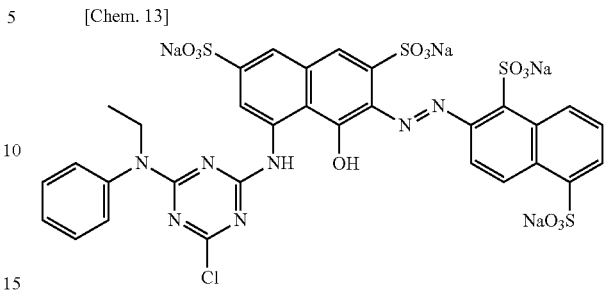

C.I. Reactive Red 31 (CAS: 12237-00-2), represented by the formula below and having a naphthalene structure substituted with one $SO_3X$ group at $R^1$ in formula (I), is not a first dye according to this embodiment. However, the ink composition according to this embodiment may contain C.I. Reactive Red 31 as a dye other than the first dye.

[Chem. 14]

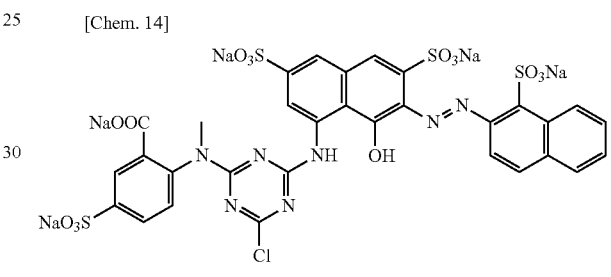

This structure of the first dye, represented by formula (I), gives the ink composition high pH stability over time and a wide range of compatibility with fabrics, allowing the user to dye different production lots of fabric with little variation in hue, whether the fabric is a cellulose fabric, such as cotton or viscose, or a polyamide fabric, such as silk or wool. Furthermore, using the first dye in combination with a second dye, described hereinafter, will lead to a wide color gamut in textile printing. These advantages appear to be based on interactions between the first and second dyes.

It is particularly preferred that one or more of C.I. Reactive Red 141, C.I. Reactive Red 24:1, and C.I. Reactive Red 245 be used as first dye(s). Although depending on the choice of second dye(s), this makes the overall pH of the ink composition more stable over time, making the ink composition more stable in terms of the hue it develops.

The first dye content of the ink composition, or the total amount of the first dyes if more than one is used, can be adjusted in order that a predetermined hue can be obtained. Typically, the first dye content is 0.1% by mass or more and 20% by mass or less of the total amount of the ink composition, preferably 1% by mass or more and 15% by mass or less, more preferably 2% by mass or more and 12% by mass or less, even more preferably 5% by mass or more and 12% by mass or less. When its first dye content is within or close to this range, the ink composition is highly stable in terms of pH, and allows for textile printing with a sufficiently wide color gamut.

1.2. Second Dye

The second dye in the ink composition according to this embodiment is represented by formula (II):

[Chem. 15]

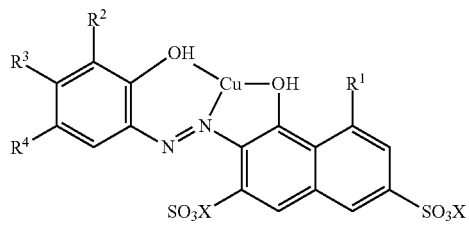

(II)

(where $R^1$ denotes $SO_3X$ or

[Chem. 16]

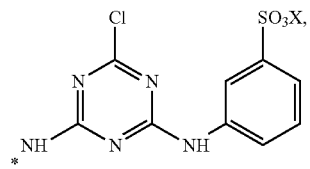

$R^2$, $R^3$, and $R^4$ each independently denote H, $SO_3X$, a halogen, or

[Chem. 17]

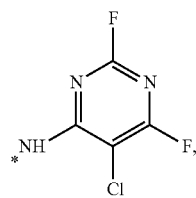

and

X denotes H, Li, Na, or K, with possible binding sites labeled with an asterisk).

If any of $R^2$, $R^3$, and $R^4$ in formula (II), which can each independently be a halogen (F, Cl, Br, or I), is a halogen, Cl is more preferred than the other halogens.

The second dye is therefore one of the several dyes available as C.I. Reactive Violet ##.

Specific examples of second dyes include C.I. Reactive Violet 1 (CAS: 12239-45-1, 69721-07-9, or 70880-03-4), represented by the formula below, and

[Chem. 18]

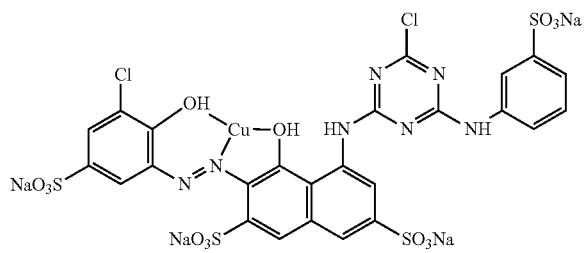

C.I. Reactive Violet 33 (CAS: 66456-81-3 or 69121-25-1), represented by the formula below.

[Chem. 19]

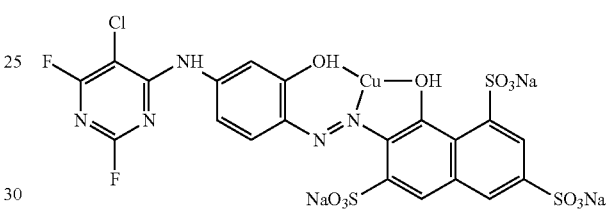

This structure of the second dye, represented by formula (II), gives the ink composition high pH stability over time and a wide range of compatibility with fabrics, allowing the user to dye different production lots of fabric with little variation in hue, whether the fabric is a cellulose fabric, such as cotton or viscose, or a polyamide fabric, such as silk or wool. Furthermore, using the second dye in combination with the first dye will lead to a wide color gamut in textile printing. These advantages appear to be based on interactions between the first and second dyes.

It is particularly preferred that one or both of C.I. Reactive Violet 1 and C.I. Reactive Violet 33 be used as second dye(s). Although depending on the choice of first dye(s), this makes the overall pH of the ink composition more stable over time, making the ink composition more stable in terms of the hue it develops.

The second dye content of the ink composition, or the total amount of the second dyes if more than one is used, can be adjusted in order that a predetermined hue can be obtained. Typically, the second dye content is 0.1% by mass or more and 10% by mass or less of the total amount of the ink composition, preferably 0.5% by mass or more and 8% by mass or less, more preferably 1% by mass or more and 5% by mass or less, even more preferably 1% by mass or more and 3% by mass or less. When its second dye content is within or close to this range, the ink composition is highly stable in terms of pH, and allows for textile printing with a sufficiently wide color gamut.

1.3. Other Ingredients 1.3.1. Water

The ink composition according to this embodiment may contain water. The water, if contained in the ink composition according to this embodiment, serves as the main liquid medium. Given that fabric to which the ink composition has been applied may be dried and any volatile component of the ink composition evaporates into the air meanwhile, it is preferred that water be used as the main medium because this makes the fabric dry faster. The water can be, for example, water free of all removable ionic impurities. Examples include types of purified water, such as ion-exchanged water, ultrafiltered water, reverse osmosis-water, and distilled water, and ultrapure water. Using sterilized water, such as ultraviolet- or hydrogen peroxide-treated water, will prevent fungal and bacterial development in the ink composition during prolonged storage.

The water content is typically 50% by mass or more of the total amount of the ink composition, preferably 55% by mass or more, more preferably 60% by mass or more, even more preferably 65% by mass or more. When the water content is 50% by mass or more, the ink composition has relatively low viscosity. As for upper limit, the water content is preferably 90% by mass or less of the total amount of the ink composition, more preferably 85% by mass or less, even more preferably 80% by mass or less. The term "aqueous ink" as used herein refers to an ink in which water constitutes 50% by mass or more of the total mass (100% by mass) of the ink.

1.3.2. Organic Solvent

The ink composition according to this embodiment may contain an organic solvent. Adding an organic solvent is a way to control the characteristics, such as viscosity and surface tension, and behavior, such as drying on fabric and penetration, of the ink composition. Water-soluble organic solvents are preferred because of their compatibility with water. The organic solvent can be, for example, a glycol or glycol ether compound.

Examples of water-soluble organic solvents include glycols, such as 1,2-pentanediol, methyl triglycol (triethylene glycol monomethyl ether), butyl triglycol (triethylene glycol monobutyl ether), butyl diglycol (diethylene glycol monobutyl ether), dipropylene glycol monopropyl ether, 1,2-hexanediol, 1,2-heptanediol, 2-methyl-3-phenoxy-1,2-propanediol, 3-(3-methylphenoxy)-1,2-propanediol, 3-hexyloxy-1,2-propanediol, 2-hydroxymethyl-2-phenoxymethyl-1,2-propanediol, ethylene glycol, diethylene glycol, triethylene glycol, polyethylene glycol, propylene glycol, dipropylene glycol, polypropylene glycol, polyoxyethylene polyoxypropylene glycol, 1,3-propane diol, 1,2-butanediol, 1,2-pentanediol, 1,4-butanediol, 1,5-pentanediol, and 1,6-hexanediol. A mixture of multiple water-soluble organic solvents can also be used.

The water-soluble organic solvent content, or the total amount of the water-soluble organic solvents if a mixture is used, is typically 0.2% by mass or more and 50% by mass or less of the total amount of the ink composition, preferably 1% by mass or more and 40% by mass or less, more preferably 5% by mass or more and 35% by mass or less, even more preferably 10% by mass or more and 30% by mass or less.

1.3.3. Surface Tension Modifier

The ink composition according to this embodiment may contain a surface tension modifier. Adding a surface tension modifier will reduce the surface tension of the ink composition, improving the wettability of the ink composition on fabric, thereby allowing the user to color the fabric with limited occurrence of faults such as uneven dyeing. The surface tension modifier can be, for example, a water-soluble organic solvent with a low surface tension or a surfactant. Examples of water-soluble organic solvents with low surface tensions include lower alcohols, such as ethanol, propanol, and butanol; diols, such as butylene glycol, 1,3-pentanediol, 2-ethyl-1,3-propanediol, and 1,6-hexanediol; and glycol monoethers, such as ethylene glycol monoethyl ether, ethylene glycol monoethyl ether, diethylene glycol monomethyl ether, diethylene glycol monoethyl ether, and propylene glycol monomethyl ether. One or more surface tension modifiers can be used.

The ink composition according to this embodiment may contain a surfactant for higher wettability on, and the resulting better penetration into, fabric. The surfactant can be selected as appropriate from, for example, nonionic, anionic, cationic, and amphoteric surfactants. Of these, acetylene glycol surfactants and silicone surfactants, highly surface-active and unlikely to produce foam, are preferred.

Examples of acetylene glycol surfactants include, but are not limited to, Olfine E1004, E1010, E1020, PD-001, PD-002 W, PD-004, PD-005, EXP. 4200, EXP. 4123, and EXP. 4300 (trade names, Nissin Chemical Industry Co., Ltd.), Surfynol 440, 465, 485, CT111, CT121, TG, and GA and Dynol 604 and 607 (trade names, Air Products Japan, Inc.), Acetylenol E40, E60, and E100 (trade names, Kawaken Fine Chemicals Co., Ltd.), Olfine 104 surfactants and Olfine E surfactants such as E1010 (trade names, Air Products Japan, Inc.), and Surfynol 465 (a trade name, Nissin Chemical Industry Co., Ltd.).

Examples of silicone surfactants include, but are not limited to, polysiloxane compounds and polyether-modified organosiloxanes. Specific examples of commercially available silicone surfactants include, but are not limited to, BYK-306, BYK-307, BYK-333, BYK-341, BYK-345, BYK-346, BYK-347, BYK-348, and BYK-349 (trade names, BYK Japan KK), KF-351A, KF-352A, KF-353, KF-354L, KF-355A, KF-615A, KF-945, KF-640, KF-642, KF-643, KF-6020, X-22-4515, KF-6011, and KF-6012 (trade names, Shin-Etsu Chemical Co., Ltd.), and Silface SAG002, 005, 503A, and 008 (trade names, Nissin Chemical Industry Co., Ltd.).

The surface tension modifier content, or the total amount of the surface tension modifiers if more than one is used, is typically 0.01% by mass or more and 5% by mass or less of the total amount of the ink composition, preferably 0.03% by mass or more and 3% by mass or less, more preferably 0.05% by mass or more and 1% by mass or less. When its surface tension modifier content falls within these ranges, the ink composition is unlikely to foam and can therefore be applied to fabric with improved wettability.

1.3.4. Moisturizing Agent

The ink composition according to this embodiment may contain a moisturizing agent. Any moisturizing agent commonly used in ink compositions for ink jetting is acceptable. A moisturizing agent may also be referred to herein as a water-attracting agent. Preferred moisturizing agents have a boiling point of 180° C. or more, more preferably 200° C. or more. Moisturizing agents with boiling points in these ranges give the ink composition high water retentivity and high moisture.

Specific examples of moisturizing agents include polyols, such as diethylene glycol, triethylene glycol, tetraethylene glycol, pentamethylene glycol, trimethylene glycol, 2-butene-1,4-diol, 2-ethyl-1,3-hexanediol, 2-methyl-2,4-pentanediol, propylene glycol, dipropylene glycol, tripropylene glycol, isobutylene glycol, glycerol, diglycerol, meso-erythritol, trimethylolpropane, pentaerythritol, and dipentaerythritol; lactams, such as 2-pyrrolidone, N-methyl-2-pyrrolidone, ε-caprolactam, and hydroxyethyl pyrrolidone; urea and its derivatives, such as thiourea, ethylene urea, and 1,3-dimethylimidazolidinone; monosaccharides, disaccharides, oligosaccharides, and polysaccharides and their derivatives, such as glucose, mannose, fructose, ribose, xylose, arabinose, galactose, aldonic acid, glucitol (sorbit), maltose, cellobiose, lactose, sucrose, trehalose, and maltotriose; and betaines, such as glycine and trimethylglycine. Of these moisturizers, diethylene glycol, triethylene glycol, propylene glycol, dipropylene glycol, and some others are also mentioned above as examples of water-soluble solvents and have the functions of both. The boiling points given herein are boiling points at 1 atm pressure.

The amount or total amount of the moisturizing agent(s), if used in the ink composition according to this embodiment, is typically 0.2% by mass or more and 10% by mass or less, preferably 0.4% by mass or more and 8% by mass or less, more preferably 0.5% by mass or more and 6% by mass or less, even more preferably 0.7% by mass or more and 5% by mass or less.

1.3.5. pH-Adjusting Agent

To the ink composition according to this embodiment, a pH-adjusting agent can be added to adjust the pH of the composition. The pH-adjusting agent can be selected from, for example, inorganic acids, organic acids, inorganic bases, organic bases, and pH buffers. Examples of inorganic acids include, but are not limited to, sulfuric acid, hydrochloric acid, and nitric acid. Preferred organic acids are carboxyl-bearing compounds. Examples include monocarboxylic acids such as formic acid, acetic acid, butyric acid, valeric acid, caproic acid, and lactic acid, dicarboxylic acids such as oxalic acid, malonic acid, succinic acid, glutaric acid, adipic acid, malic acid, and tartaric acid, tricarboxylic acids such as propionic acid, butyric acid, oxalic acid, and malonic acid, and tricarboxylic acids such as citric acid, succinic acid, and fumaric acid. Examples of inorganic bases include lithium hydroxide, sodium hydroxide, potassium hydroxide, and ammonia. Examples of organic bases include triethanolamine, diethanolamine, monoethanolamine, tripropanolamine, triisopropanolamine, diisopropanolamine, and tris(hydroxymethyl)aminomethane. Examples of pH buffers include phosphate buffer, citrate buffer, and tris buffer.

pH-adjusting agents can be used alone or in combination, preferably in combination. For example, a combination of an organic acid and an organic base is preferred. With such a combination, it is easier to adjust the pH of the ink composition to the desired level. The pH-adjusting agent content, or the total amount of the pH-adjusting agents if a combination is used, is typically 0.01% by mass or more and 1.0% by mass or less of the total amount of the ink composition, preferably 0.1% by mass or more and 0.6% by mass or less, more preferably 0.2% by mass or more and 0.5% by mass or less.

A pH-adjusting agent added to the ink makes it more stable and better in maintaining its pH in the desired range, even when left under conditions under which its pH is likely to change, such as a long period of storage. Such an ink is stable in terms of the hue it develops on prints made therewith, helping the user dye fabric with high fidelity to the designed color. By virtue of the pH stability higher than without a pH-adjusting agent, furthermore, such an ink composition can be used with an ink jet recording device only causing acceptably limited damage to the device, such as corrosion of a recording head.

1.3.6. Other Ingredients

The ink composition according to this embodiment may optionally contain other various additives, such as dyes other than first or second dyes, preservatives, dissolution aids, viscosity modifiers, antioxidants, antimolds, chelating agents, antioxidants, ultraviolet absorbers, oxygen absorbers, and resin particles.

Although the above sections about water-soluble solvents and moisturizing agents list some polyhydric alcohols, it is preferred that the ink composition according to this embodiment contain no or up to 5% by mass, of the total amount of the ink, polyhydric alcohols with boiling points higher than 260° C., more preferably no or up to 3% by mass, even more preferably no or up to 1% by mass. This allows the user to color fabric darker than usual by virtue of the small number of alcoholic hydroxyl groups, a cause of incomplete fixation of dyes in the process of dyeing. This can be described in more detail as follows. The driving force of the fixation of a dye is a reaction between the reactive groups of the dye and hydroxyl groups that vegetable fiber, for example, has. Any alcoholic hydroxyl group can also react with the reactive groups of the dye as with the hydroxyl groups that vegetable fiber, for example, has. If abundant in the ink composition, therefore, alcoholic hydroxyl groups can inhibit the fixation of the dye. However, even if a polyhydric alcohol, an alcohol having two or more hydroxyl groups, is contained in the ink composition, the polyhydric alcohol evaporates quickly, leaving little after the ink composition is applied to the fabric, as long as its boiling point is 260° C. or less. As a result, the number of alcoholic hydroxyl groups left in the ink composition applied to the fabric is small, and it is unlikely that the reaction between the reactive groups of the dye and the hydroxyl groups that vegetable fiber, for example, has is inhibited. The dye is fixed in a stable manner, allowing the user to color the fabric with limited occurrence of faults such as uneven dyeing. Examples of polyhydric alcohols with boiling points higher than 260° C. include triethylene glycol (287° C.), tetraethylene glycol (314° C.), tripropylene glycol (273° C.), and glycerol (290° C.).

1.4. Characteristics of the Ink Composition

Mixing the above ingredients in any order and optionally eliminating impurities from the mixture by, for example, filtration gives an ink composition according to this embodiment. In a mixing method suitable for this embodiment, the ingredients are sequentially added to a vessel equipped with a stirrer, such as a mechanical stirrer or a magnetic stirrer, and stirred and mixed in the vessel.

For a good balance between recording quality and reliability for use as an ink for ink jet recording, it is preferred that the ink composition according to this embodiment have a surface tension of 10 mN/m or more and 40 mN/m or less at 25° C., more preferably 25 mN/m or more and 40 mN/m or less. When its surface tension at 25° C. falls within these ranges, the ink composition can be ejected with improved stability in ink jetting-based textile printing, and, if used to dye fabric to draw an image or any other design thereon, is capable of forming the image with high resolution. The surface tension of the ink composition can be determined using CBVP-Z automated surface tensiometer (Kyowa Interface Science Co., Ltd.), specifically by immersing part of a platinum plate in the ink composition and measuring the surface tension at 25° C.

For the same reason, it is preferred that the ink composition have a viscosity of 2 mPa·s or more and 15 mPa·s or less at 20° C., more preferably 2 mPa·s or more and 5 mPa·s or less, even more preferably 2 mPa·s or more and 4.5 mPa·s or less. The viscosity of the ink composition can be measured using MCR-300 rheometer (Physica), by increasing the shear rate from 10 to 1000 and reading the viscosity at a shear rate of 200 at 20° C.

The pH of the ink composition according to this embodiment is preferably 6.0 or more and 8.5 or less, more preferably 6.5 or more and 8.5 or less, even more preferably 7.0 or more and 8.0 or less. It is preferred that the pH of the ink composition remain in these ranges during both the post-production and storage periods. As used herein, the post-production period refers to 24 hours after the ingredients of the ink composition are blended, and the storage period refers to the period from loading into an ink container, such as an ink cartridge, to ejection from an ink jet recording head. For example, the storage period may refer to the warranty period of the ink cartridge. An estimated pH during the storage period obtained through an accelerated study at a high temperature, approximately 60° C., can also be used.

When its pH falls within these ranges, the ink composition is more stable than usual in terms of the hue it develops on the images it forms, by virtue of its improved stability over time, allowing the user to print a predetermined design on fabric in the user's intended tone with less variation in hue. The pH of the ink composition can be adjusted to fall within these ranges by adding a pH-adjusting agent as mentioned above.

1.5. Operations and Advantages

The ink composition according to this embodiment is stable over time in terms of pH by virtue of the appropriate chemical structure of the first and second dyes, and, when used in textile printing, gives prints high color strength. The ink composition according to this embodiment has a wide range of compatibility with fabrics too, allowing the user to dye different production lots of fabric with little variation in hue, whether the fabric is a cellulose fabric, such as cotton or viscose, or a polyamide fabric, such as silk or wool. The chemical structure of the first and second dyes is highly resistant to light and will give high light fastness to prints made using the ink composition. The ink composition helps obtaining the desired hue, especially in the violet gamut. When used as a component of an ink set, furthermore, the ink composition according to this embodiment allows the user to perform textile printing with a wide color gamut.

When containing a pH-adjusting agent, the ink composition is more stable than usual in terms of the hue it develops on the images it forms, even when subjected to conditions under which its pH is likely to change, such as a long period of storage, allowing the user to dye fabric to the user's intended color tone and design. When the ink composition contains no or up to 5% by mass, of the total amount of the ink, polyhydric alcohols with boiling points higher than 260° C., furthermore, it gives fabric a color darker than usual by virtue of the small number of alcoholic hydroxyl groups and the consequent limited inhibition of fixation of the dyes.

2. Ink Set

An ink set according to this embodiment includes an above-described ink composition (as a magenta ink composition, for example), a yellow ink composition containing C.I. Reactive Yellow 95 or C.I. Reactive Yellow 2, a cyan ink composition containing C.I. Reactive Blue 72 or C.I. Reactive Blue 15:1, and a black ink composition containing C.I. Reactive Black 39.

The yellow ink composition may contain various ingredients, such as dyes other than C.I. Reactive Yellow 95 and 2, water, organic solvents, surface tension modifiers, pH-adjusting agents, preservatives, dissolution aids, viscosity modifiers, antioxidants, antimolds, chelating agents, and resin particles. The same details as in the above section about an ink composition apply to the water, organic solvents, surface tension modifiers, pH-adjusting agents, preservatives, dissolution aids, viscosity modifiers, antioxidants, antimolds, chelating agents, and resin particles that can be used in the yellow ink composition. Examples of dyes that can be used in the yellow ink composition include C.I. Reactive Yellow 2, 7, 15, 22, 37, 42, 57, 69, 76, 81, 95, 102, 125, and 135. C.I. Reactive Yellow 95 is preferred, as it is stable in terms of hue and has a wide range of compatibility with fabrics when used with a magenta ink according to an aspect of the invention.

The cyan ink composition may contain various ingredients, such as dyes other than C.I. Reactive Blue 72 and 15:1, water, organic solvents, surface tension modifiers, pH-adjusting agents, preservatives, dissolution aids, viscosity modifiers, antioxidants, antimolds, chelating agents, and resin particles. The same details as in the above section about an ink composition apply to the water, organic solvents, surface tension modifiers, pH-adjusting agents, preservatives, dissolution aids, viscosity modifiers, antioxidants, antimolds, chelating agents, and resin particles that can be used in the cyan ink composition. Examples of dyes that can be used in the cyan ink composition include C.I. Reactive Blue 2, 13, 15:1, 21, 38, 41, 50, 69, 72, 109, 120, and 143. C.I. Reactive Blue 72 and 15:1 are preferred, as they are stable in terms of hue and have a wide range of compatibility with fabrics when used with a magenta ink according to an aspect of the invention.

The black ink composition may contain various ingredients, such as dyes other than C.I. Reactive Black 39, water, organic solvents, surface tension modifiers, pH-adjusting agents, preservatives, dissolution aids, viscosity modifiers, antioxidants, antimolds, chelating agents, and resin particles. The same details as in the above section about an ink composition apply to the water, organic solvents, surface tension modifiers, pH-adjusting agents, preservatives, dissolution aids, viscosity modifiers, antioxidants, antimolds, chelating agents, and resin particles that can be used in the black ink composition. Examples of dyes that can be used in the black ink composition include C.I. Reactive Black 3, 4, 5, 8, 13, 14, 31, 34, 35, and 39. C.I. Reactive Black 39 is preferred, as it is stable in terms of hue and has a wide range of compatibility with fabrics when used with a magenta ink according to an aspect of the invention.

The dye content of each ink composition can be adjusted as appropriate according to the purpose of use. Preferably, the dye content of each ink composition is 0.10% by mass or more and 20.0% by mass or less, more preferably 0.20% by mass or more and 15.0% by mass or less, even more preferably 1.0% by mass or more and 10.0% by mass or less.

Such an ink set, when including an above-described ink composition according to this embodiment as a magenta ink composition, allows the user to dye different production lots of fabric with little variation in the hue of each ink, whether the fabric is a cellulose fabric, such as cotton or viscose, or a polyamide fabric, such as silk or wool. With such an ink set the user can also perform textile printing with an extended color gamut. By using an above-described ink composition according to this embodiment as a magenta ink composition, the user can produce recordings with a wide range of compatibility with fabrics.

3. Ink Jet Recording Device

The following describes an ink jet recording device according to this embodiment with reference to FIG. 1. An ink jet recording device colors pieces of fabric (produces recordings) by ink jetting, i.e., ejecting tiny droplets of ink compositions to hit the portions to be colored of the pieces of fabric. FIG. 1 is a schematic perspective view of an ink jet recording device according to an embodiment. This embodiment describes a cartridge-on-carriage printer, which has ink cartridges on a carriage, as an example of an ink jet recording device. In FIG. 1, the components are not to scale so that they are large enough to be recognized.

The printer 1, described as an ink jet recording device according to this embodiment, is what is called a serial printer. A serial printer has a carriage that moves in a predetermined direction and a head supported by the carriage. The carriage carries the head, and meanwhile the head performs printing. Instead of a serial printer, the recording device can also be a line printer.

As illustrated in FIG. 1, the printer 1 has components such as a head 3 as an ink jet recording head, a carriage 4, a primary scanning mechanism 5, a platen roller 6, and a control unit (not illustrated) that controls the overall operation of the printer 1. The carriage 4 supports the head 3 and detachable ink cartridges 7a, 7b, 7c, and 7d that contain inks to be supplied to the head 3.

The primary scanning mechanism 5 has a timing belt connected to the carriage 4, a motor 9 that drives the timing belt 8, and a guide shaft 10. The guide shaft 10 extends in the direction of the movement of the carriage 4 (the primary scanning direction), supporting the carriage 4. The motor 9 drives the carriage 4 via the timing belt 8 to move back and forth along the guide shaft 10. In this way, the primary scanning mechanism 5 moves the carriage 4 back and forth in the primary scanning direction.

The platen roller 6 transports a recording medium 2, a piece of fabric as the substrate for textile printing, in a secondary scanning direction perpendicular to the primary scanning direction (the direction along the length of the recording medium 2). The recording medium 2 is therefore transported in the secondary scanning direction. The primary scanning direction, in which the carriage 4 moves back and forth carrying the head 3, substantially corresponds to the direction along the width of the recording medium 2; therefore, the head 3 scans the recording medium 2 in the primary and secondary scanning directions as the relative positions of these two components change.

The four separate ink cartridges 7a, 7b, 7c, and 7d, capable of storing above-described ink compositions, individually contain color ink compositions, such as black, cyan, magenta, and yellow ink compositions, and can be used in any combination. Although there are four in FIG. 1, any number of ink cartridges can be used. The ink cartridges 7a, 7b, 7c, and 7d each have a bottom port (not illustrated) through which the ink composition stored in the ink cartridge is supplied to the head 3.

Figure 2:
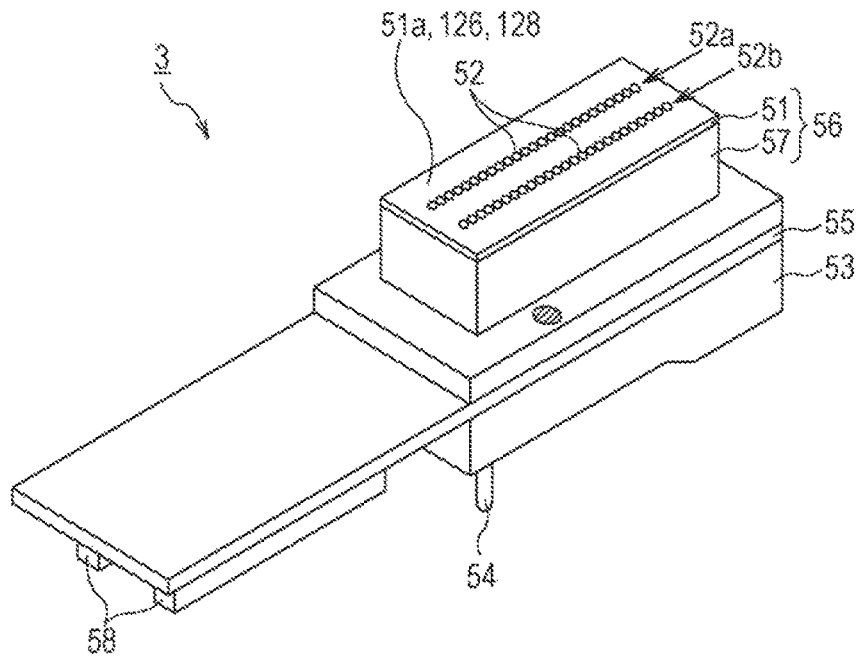
FIG. 2 is a schematic perspective view of an ink jet recording head.

The following describes the configuration of the head 3 with reference to FIG. 2. FIG. 2 is a schematic perspective view of an ink jet recording head.

As illustrated in FIG. 2, the head 3 has components such as an inlet section 53, a head substrate 55, and a main body 56. The inlet section 53, through which an ink composition is introduced into the head 3, is fitted with a connection needle 54. The connection needle 54 is connected to the bottom port of each ink cartridge and delivers the ink composition into the head 3.

The head substrate 55 is positioned with one side thereof contiguous to the inlet section 53 and the other side facing the main body 56. The head substrate 55 is fitted with a dual connector 58, at which the head 3 is electrically coupled with a circuit board (not illustrated) via a flexible flat cable (not illustrated).

The main body 56, contiguous to the head substrate 55, incorporates a passage for the ink composition coming from the connection needle 54 to flow through. The components of the main body 56 include a pressurizing section 57 and a nozzle plate 51. The pressurizing section contains piezoelectric elements as drivers (actuators) for the head 3 in cavities (not illustrated). The nozzle plate 51 can be made of any material. To name a few, stainless steel (e.g., SUS) and polyimide can be used.

The side of the nozzle plate 51 from which the head 3 ejects the ink composition is a nozzle surface 51a. On the nozzle surface 51a are two parallel nozzle rows 52a and 52b, each formed by multiple, regularly spaced nozzles 52. Having these two nozzle rows 52a and 52b, the head 3 is a so-called dual-nozzle head. The nozzles 52, round and measuring approximately 30 µm in diameter, are in one-to-one correspondence with the cavities. The nozzle surface 51a is covered with a plasma-polymerized coating 126 and a fluoropolymer coating 128, both described hereinafter.

In this configuration, an ink supply mechanism supplies the head 3 with an ink composition, loading the head 3 with the ink composition. A head driver (not illustrated) then applies a driving signal (electric signal) to the piezoelectric elements in the head 3. The piezoelectric elements deform, changing the volume of the cavities in the pressurizing section 57. The pumping effect of these changes in volume pressurizes the ink composition in the cavities. As a result, the ink composition is ejected through the nozzles 52.

The drivers (actuators) for the head 3, provided in one-to-one correspondence with the nozzles 52, do not need to be piezoelectric elements. The drivers can be, for example, electromechanical transducers, which displace a diaphragm as an actuator using electrostatic attraction, or electrothermal transducers, which eject droplets of an ink composition using bubbles generated by heating.

Nozzle Plate

The nozzle plate 51 contains fluorine in at least part of its surface (the nozzle surface 51a) and has siloxane bonds less than 1 µm beneath the surface. The surface of the nozzle plate 51 includes any coating formed at least partially on the surface of the nozzle plate 51 by a physical or chemical treatment in order to change the nature of the surface.

Figure 3:
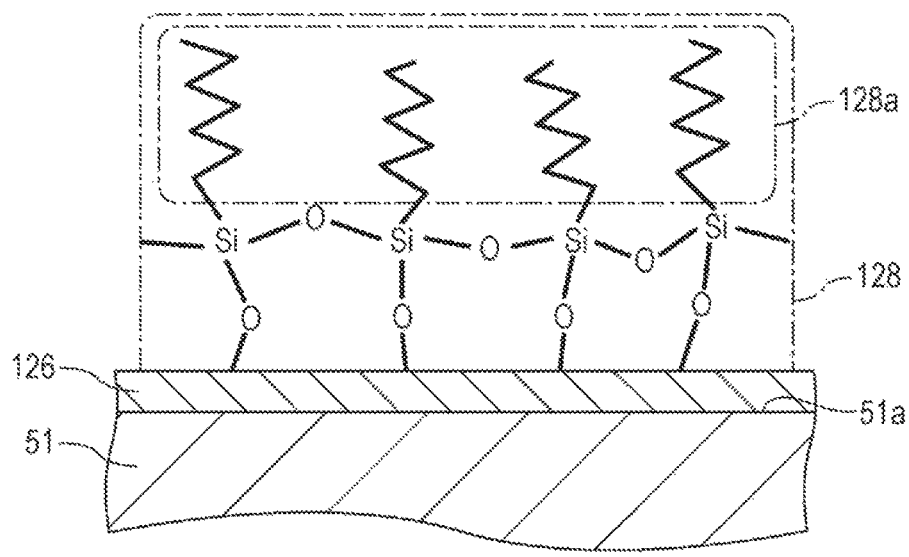
FIG. 3 is a conceptual illustration of the surface of a nozzle plate.

When the nozzle plate 51 is a stainless-steel plate, plasma-polymerizing a silicone material on the surface of the nozzle plate 51 and the inner surfaces of the nozzles 52 gives a plasma-polymerized coating 126 (see FIG. 3). The plasma-polymerized coating 126 can be made of, for example, silicone oil or an alkoxysilane, such as dimethylpolysiloxane. Specific examples of commercially available materials that can be used include TSF451 (GE Toshiba Silicones) and SH200 (Dow Corning Toray Silicone).

On the surface of the plasma-polymerized coating 126 is a liquid-repellent fluoropolymer coating 128 (see FIG. 3), preferably a monolayer of an alkoxysilane having fluorine-containing long polymer chains. The fluorine-containing long polymer chains can be, for example, perfluoroalkyl or perfluoropolyether chains with molecular weights of 1000 or more. An example of an alkoxysilane having long polymer chains is a silane coupling agent having long polymer chains. An example of such a silane coupling agent is heptatriacontafluoroicosyltrimethoxysilane, and commercially available ones include Optool DSX (a trade name, Daikin Industries) and KY-130 (a trade name, Shin-Etsu Chemical). When the nozzle plate 51 is a polyimide plate, the fluoropolymer coating 128 can be formed on the surface of the nozzle plate 51 directly, without the plasma-polymerized coating 126 underneath.

The following describes the surface condition of the nozzle plate 51 with reference to FIG. 3. FIG. 3 is a conceptual illustration of the surface of a nozzle plate.

On the surface of the nozzle plate 51 (nozzle surface 51*a*) in FIG. 3 are a plasma-polymerized coating 126 and a fluoropolymer coating 128 on the plasma-polymerized coating 126, the fluoropolymer coating 128 containing fluorine-containing long polymer chains 128*a*. Immersing a nozzle plate 51 with a plasma-polymerized coating 126 thereon in a solution of an alkoxysilane having fluorine-containing long polymer chains gives a fluoropolymer coating 128, a layer of a polymer of the alkoxysilane having fluorine-containing long polymer chains, on the surface of the plasma-polymerized coating 126. The silicon atoms in the fluoropolymer coating 128 bind with the plasma-polymerized coating 126 with oxygen atoms therebetween (forming what is called siloxane bonds). As a result, the fluorine-containing long polymer chains 128*a* are clustered on the outer side. In this way, at least part of the surface of the nozzle plate 51 (nozzle surface 51*a*) of the head 3 contains fluorine derived from a fluoropolymer coating 128, a monolayer.

As a result, siloxane bonds sit less than 1 μm beneath the outermost surface of the nozzle plate 51. In this configuration, silicone atoms in the fluoropolymer coating 128 bind three-dimensionally with each other, entangling the fluorine-containing long polymer chains. This gives the fluoropolymer coating 128 a high density and makes the coating repellent and less permeable to the ink composition, improving the resistance of the fluoropolymer coating 128 and the plasma-polymerized coating 126 to corrosion by the ink composition.

Another method for bringing fluorine into at least part of the surface of the nozzle plate 51 is to form a co-deposition plating of nickel ions and a fluoropolymer on the surface of the nozzle plate 51, whether by electrolytic or electroless plating. A specific but not the only example of a preferred method is to immerse the nozzle plate in an electrolytic solution in which nickel ions and liquid-repellent polymer particles have been dispersed using electric charge and then stir the electrolytic solution to form co-deposition plating on the surface of the nozzle plate. The liquid-repellent polymer particles, a material for the co-deposition plating, are preferably particles of a polymer such as polytetrafluoroethylene (PTFE), polyperfluoroalkoxybutadiene, polyfluorovinylidene, polyfluorovinyl, or polydiperfluoroalkylfumarate or mixed particles of such polymers. The metal, another material for the co-deposition plating, does not need to be nickel. A metal selected as appropriate from copper, silver, tin, and zinc, to name a few, can also be used. For use as the metal as a material for the co-deposition plating, materials that have large surface hardness and superior wear resistance, such as nickel, nickel-cobalt alloys, and nickel-boron alloys, are more preferred than materials that do not.

4. Recording Method

The following describes a recording method according to this embodiment. The recording method according to this embodiment includes ejecting an above-described ink composition from a commonly used ink jet recording head, preferably from a head 3 that has a nozzle plate 51 containing fluorine in at least part of its surface and having siloxane bonds less than 1 μm beneath the surface. The method, furthermore, includes at least loading an above-described ink composition into an ink jet recording head (hereinafter also referred to simply as "a head") of an ink jet recording device (an ink jet printer) and attaching the ink composition to a piece of fabric by ink jetting. The head may have been loaded with the ink compositions in an above-described ink set. For example, an above-described ink composition according to this embodiment as a magenta ink composition and cyan, yellow, and black ink compositions may be assigned to different rows of nozzles of the head.

The attachment of the ink composition to a piece of fabric by ink jetting includes ejecting droplets of the ink composition from nozzles of the head to hit the piece of fabric, thereby forming (printing) a design, such as an image, text, a pattern, or a color, on the piece of fabric. The piece of fabric is then subjected to any treatment deemed appropriate, such as heating, to give a print (recording), a piece of fabric with the design printed (recorded) with the ink composition.

The ink jet recording device used in this embodiment ejects an ink composition in the form of droplets from its head 3 (see FIG. 2). The droplets are ejected intermittently with predetermined intervals and have a predetermined volume (mass). As a result, droplets of the ink composition hit a piece of fabric, forming a predetermined image or any other design.

The amount of ink composition applied to the piece of fabric is preferably 1.5 $mg/cm^2$ or more and 6 $mg/cm^2$ or less, more preferably 2 $mg/cm^2$ or more and 5 $mg/cm^2$ or less. When 1.5 $mg/cm^2$ or more is attached, the ink composition tends to be superior in color strength on the image recorded (printed). When 6 $mg/cm^2$ or less is attached, the droplets of the ink composition dry faster on the piece of fabric, limiting bleeding in the recorded (printed) image or other design.

The recording method according to this embodiment may include heating the ink composition (image) applied to the piece of fabric.

Examples of methods for heating the ink composition attached to the piece of fabric include, but are not limited to, heat pressing, atmospheric steaming, pressure steaming, and thermofixing. Any kind of heat source can be used, and an example is infrared radiation (an infrared lamp).

The heating temperature, at which the ink composition on the piece of fabric is heated, is not critical. Preferably, the heating temperature is 150° C. or more and 200° C. or less, more preferably 160° C. or more and 180° C. or less. At temperatures in these ranges, the heating process promotes the reaction, drying, fixing, etc., of the ink composition with limited thermal damage to the piece of fabric. The heating temperature as mentioned herein refers to the temperature to which the surface of the image or other design formed on the piece of fabric is heated, and can be measured using, for example, a non-contact thermometer (trade name, "IT2-80"; Keyence Corporation). The heating time, for which the ink composition is exposed to the heating temperature, is not critical either. For example, the heating time can be 30 seconds or more and 20 minutes or less.

The recording method according to this embodiment records (prints) a design on a medium (fabric) that can be dyed with an above-described ink composition. Examples of such media include, but are not limited to, fabrics made from vegetable fiber, such as cotton or hemp; fabrics made from animal fiber, such as silk or wool; fabrics made from synthetic fiber, such as polyester, acetate, triacetate, polyamide, or polyurethane; fabrics made from biodegradable fiber, such as polylactic acid; and fabrics made from a blend of these fibers. Fabric refers to a woven form, knitted form, nonwoven sheet, or other sheet-shaped form of any such fiber. For use as the fabric in the recording method according to this embodiment, those made from cellulose-containing vegetable fiber, such as cotton or hemp, are more preferred than others. Using these fabrics will lead to improved dyeability (fastness). The weight of the piece of fabric used in this embodiment is not critical. Typically, the weight of the piece of fabric is 1.0 oz (ounce) or more and 10.0 oz or less, preferably 2.0 oz or more and 9.0 oz or less, more preferably 3.0 oz or more and 8.0 oz or less, even more preferably 4.0 oz or more and 7.0 oz or less.

5. Examples and Comparative Examples

The following describes an aspect of the invention in more detail by providing examples. No aspect of the invention is limited to these examples.

5.1. Preparation of Ink Compositions

Ink compositions were prepared by mixing the ingredients (materials) as set forth in Table 1, 2, or 3, thoroughly stirring the mixture to homogeneity, and filtering the resulting blend through a membrane filter (pore size, 1 μm). The values in Tables 1, 2, and 3 are in % by mass, with the total being 100% by mass.

TABLE 1

| | | | Example 1 | 2 | 3 | 4 | 5 | 6 | 7 | 8 | 9 | 10 |
|---|---|---|---|---|---|---|---|---|---|---|---|---|
| | | Ink | Ink 1 | Ink 2 | Ink 3 | Ink 4 | Ink 5 | Ink 6 | Ink 7 | Ink 8 | Ink 9 | Ink 10 |
| Formula of the ink composition | First dye(s) | RR24:1 | 10 | — | — | 9 | — | — | 9.5 | — | — | 10.5 |
| | | RR141 | — | 10 | — | — | 9 | — | — | 9.5 | — | — |
| | | RR245 | — | — | 10 | — | — | 9 | — | — | 9.5 | — |
| | Second dye(s) | RV1 | 1 | 1 | 1 | — | — | — | 1 | 1 | 1 | — |
| | | RV33 | — | — | — | 1 | 1 | 1 | — | — | — | 2 |
| | Other dye(s) | RR31 | — | — | — | — | — | — | — | — | — | — |
| | | AR138 | — | — | — | — | — | — | — | — | — | — |
| | | AV97 | — | — | — | — | — | — | — | — | — | — |
| | Water-soluble solvents | 1,2-Hexanediol (223° C.) | 3 | 3 | 3 | 3 | 3 | 3 | 3 | 3 | 3 | 3 |
| | | Propylene glycol (188° C.) | 10 | 10 | 10 | 10 | 10 | 10 | 10 | 10 | 10 | 10 |
| | | 2-Pyrrolidone (245° C.) | 10 | 10 | 10 | 10 | 10 | 10 | 10 | 10 | 10 | 10 |
| | | Glycerol (290° C.) | — | — | — | — | — | — | — | — | — | — |
| | Water-attracting agent | Urea | 3 | 3 | 3 | 3 | 3 | 3 | 3 | 3 | 3 | 3 |
| | Surfactant | Olfine PD002W | 0.2 | 0.2 | 0.2 | 0.2 | 0.2 | 0.2 | 0.2 | 0.2 | 0.2 | 0.2 |
| | pH-adjusting agents | Triethanolamine | 0.3 | 0.3 | 0.3 | 0.3 | 0.3 | 0.3 | — | — | — | — |
| | | Tripropanolamine | — | — | — | — | — | — | 0.3 | 0.3 | 0.3 | 0.3 |
| | | Adipic acid | 0.05 | 0.05 | 0.05 | 0.05 | 0.05 | 0.05 | 0.05 | 0.05 | 0.05 | 0.05 |
| | Water | Ion-exchanged water | Balance | Balance | Balance | Balance | Balance | Balance | Balance | Balance | Balance | Balance |
| | | Total | 100 | 100 | 100 | 100 | 100 | 100 | 100 | 100 | 100 | 100 |
| Characteristics | | Ink pH | 8.1 | 8.2 | 8.4 | 8.2 | 8.3 | 8.5 | 8.2 | 8.3 | 8.4 | 7.8 |
| Evaluation results | Storage stability | (pH stability) | A | A | A | A | A | A | A | A | A | B |
| | Color strength | Cotton | A | A | A | A | A | A | A | A | A | A |
| | | Silk | A | A | A | A | B | B | A | A | A | A |
| | Hue variability | (Cotton vs. silk) | B | B | A | B | B | B | A | A | A | C |
| | Light durability | Cotton | B | A | A | A | A | A | B | A | A | B |
| | | Silk | B | B | A | B | A | A | B | A | A | C |

TABLE 2

| | | | Example 11 | 12 | 13 | 14 | 15 | 16 | 17 | 18 | 19 | 20 | 21 |
|---|---|---|---|---|---|---|---|---|---|---|---|---|---|
| | | Ink | Ink 11 | Ink 12 | Ink 13 | Ink 14 | Ink 15 | Ink 16 | Ink 17 | Ink 18 | Ink 19 | Ink 20 | Ink 21 |
| Formula of the ink composition | First dye(s) | RR24:1 | — | — | 10 | — | — | — | — | 8 | — | 2 | 2 |
| | | RR141 | 10.5 | — | — | 10 | — | — | — | 2 | 8 | — | 3 |
| | | RR245 | — | 10.5 | — | — | 10 | 10 | 10 | — | 2 | 8 | 5 |
| | Second dye(s) | RV1 | — | — | 1 | 1 | 1 | 1 | 1 | 0.6 | 0.6 | 0.6 | 0.6 |
| | | RV33 | 2 | 2 | — | — | — | — | — | 0.4 | 0.4 | 0.4 | 0.4 |
| | Other dye(s) | RR31 | — | — | — | — | — | — | — | — | — | — | — |
| | | AR138 | — | — | — | — | — | — | — | — | — | — | — |
| | | AV97 | — | — | — | — | — | — | — | — | — | — | — |
| | Water-soluble solvents | 1,2-Hexanediol (223° C.) | 3 | 3 | 3 | 3 | 3 | 3 | 3 | 3 | 3 | 3 | 3 |
| | | Propylene glycol (188° C.) | 10 | 10 | 10 | 10 | 10 | 10 | 10 | 10 | 10 | 10 | 10 |
| | | 2-Pyrrolidone (245° C.) | 10 | 10 | 10 | 10 | 10 | 10 | 10 | 10 | 10 | 10 | 10 |
| | | Glycerol (290° C.) | — | — | — | — | — | 5 | 8 | — | — | — | — |
| | Water-attracting agent | Urea | 3 | 3 | 3 | 3 | 3 | 3 | 3 | 3 | 3 | 3 | 3 |

TABLE 2-continued

| | | | \multicolumn{11}{c}{Example} |
|---|---|---|---|---|---|---|---|---|---|---|---|---|---|
| | | | 11 | 12 | 13 | 14 | 15 | 16 | 17 | 18 | 19 | 20 | 21 |
| | Surfactant | Olfine PD002W | 0.2 | 0.2 | 0.2 | 0.2 | 0.2 | 0.2 | 0.2 | 0.2 | 0.2 | 0.2 | 0.2 |
| | pH-adjusting agents | Triethanolamine | — | — | 0.1 | 0.1 | 0.1 | 0.1 | 0.1 | 0.3 | 0.3 | 0.3 | 0.3 |
| | | Tripropanolamine | 0.3 | 0.3 | — | — | — | — | — | — | — | — | — |
| | | Adipic acid | 0.05 | 0.05 | 0.05 | 0.05 | 0.05 | 0.05 | 0.05 | 0.05 | 0.05 | 0.05 | 0.05 |
| | Water | Ion-exchanged water | Balance | Balance | Balance | Balance | Balance | Balance | Balance | Balance | Balance | Balance | Balance |
| | | Total | 100 | 100 | 100 | 100 | 100 | 100 | 100 | 100 | 100 | 100 | 100 |
| Characteristics | | Ink pH | 7.9 | 7.9 | 6.6 | 6.7 | 6.8 | 6.8 | 6.8 | 8.2 | 8.2 | 8.4 | 8.3 |
| Evaluation results | Storage stability | (pH stability) | B | B | A | A | A | A | A | A | A | A | A |
| | Color strength | Cotton | A | A | A | A | A | B | C | A | A | A | A |
| | | Silk | A | A | A | A | A | B | C | A | B | B | A |
| | Hue variability | (Cotton vs. silk) | C | B | B | B | A | A | A | B | B | B | B |
| | Light durability | Cotton | A | B | B | A | A | A | A | A | A | A | A |
| | | Silk | C | C | B | B | A | A | A | B | A | A | B |

TABLE 3

| | | | \multicolumn{5}{c}{Comparative Example} |
|---|---|---|---|---|---|---|---|
| | | | 1 | 2 | 3 | 4 | 5 |
| | | Ink | Ink 22 | Ink 23 | Ink 24 | Ink 25 | Ink 26 |
| Formula of the ink composition | First dye(s) | RR24:1 | — | — | — | 10 | — |
| | | RR141 | — | — | — | — | — |
| | | RR245 | — | — | — | — | — |
| | Second dye(s) | RV1 | — | — | — | — | 10 |
| | | RV33 | — | — | — | — | — |
| | Other dye(s) | RR31 | 10 | 12.5 | — | — | — |
| | | AR138 | — | — | 10 | — | — |
| | | AV97 | — | — | 1 | — | — |
| | Water-soluble solvents | 1,2-Hexanediol (223° C.) | 3 | 3 | 3 | 3 | 3 |
| | | Propylene glycol (188° C.) | 10 | 10 | 10 | 10 | 10 |
| | | 2-Pyrrolidone (245° C.) | 10 | 10 | 10 | 10 | 10 |
| | | Glycerol (290° C.) | — | — | — | — | — |
| | Water-attracting agent | Urea | 3 | 3 | 3 | 3 | 3 |
| | Surfactant | Olfine PD002W | 0.2 | 0.2 | 0.2 | 0.2 | 0.2 |
| | pH-adjusting agents | Triethanolamine | 0.3 | — | 0.3 | 0.3 | 0.3 |
| | | Tripropanolamine | — | 0.3 | — | — | — |
| | | Adipic acid | 0.05 | 0.05 | 0.05 | 0.05 | 0.05 |
| | Water | Ion-exchanged water | Balance | Balance | Balance | Balance | Balance |
| | | Total | 100 | 100 | 100 | 100 | 100 |
| Characteristics | | Ink pH | 8.0 | 8.1 | 8.0 | 8.1 | 8.1 |
| Evaluation results | Storage stability | (pH stability) | D | D | C | A | A |
| | Color strength | Cotton | C | A | D | B | B |
| | | Silk | D | A | C | B | B |
| | Hue variability | (Cotton vs. silk) | C | D | D | D | D |
| | Light durability | Cotton | B | B | D | B | B |
| | | Silk | D | D | D | B | B |

In the tables, "RR," "RV," "AR," and "AV" stand for "Reactive Red," "Reactive Violet," "Acid Red," and "Acid Violet," respectively. Olfine PD002 W is an acetylene glycol surfactant (a trade name, Nissin Chemical Industry Co., Ltd.). The other ingredients were commercially available reagents. The temperatures in parentheses that follow the names of water-soluble solvents in Tables 1, 2, and 3 are the boiling points of the solvents.

5.2. Storage Stability Evaluation

The obtained ink compositions were stored in sampling bottles at 60° C. for 7 days. On the basis of the pH levels measured before storage (immediately after preparation) and after storage and the difference, storage stability was graded against the criteria given below. The results are presented in Tables 1, 2, and 3. Storage stability was assessed as acceptable if the grade according to the following criteria was A or B.

A: The change in pH is less than 1, and the pH measured after storage is 6 or more.

B: The change in pH is 1 or more and less than 2, and the pH measured after storage is 6 or more.

C: The change in pH is 2 or more, and the pH measured after storage is 6 or more.

D: The pH measured after storage is less than 6.

5.3. Color Strength Evaluation

Each of the obtained ink compositions was loaded into the yellow cartridge of PX-G930 ink jet printer (Seiko Epson Corporation), and a solid pattern was printed on pieces of fabric 1 (100% cotton; grammage, 130 g/m²) and fabric 2 (100% silk, grammage, 90 g/m²), each pretreated, with a series of ink ejection volumes from 5% to 100% duty. The resolution of the image was 1440×720 dpi. The parameter % duty is herein defined as the number of dots recorded per square inch/(vertical resolution×horizontal resolution)×100.

The pieces of fabric printed with the ink composition were steamed at 102° C. for 10 minutes, washed with a 0.2% by mass aqueous solution of Laccol STA (Meisei Chemical Works, Ltd.) at 90° C. for 10 minutes, and dried.

The hue of the resulting evaluation samples was evaluated as follows. The L*, a*, and b* values of the image were measured using a spectrodensitometer (trade name, "Spectrolino"; X-Rite) under the following conditions: light source, D65; status, DIN_NB; angle of view, 2 degrees; filter, UV. For each sample, color strength (C*) was calculated according to the equation below. On the basis of the maximum (C*max) for each fabric, color strength was graded against the criteria below. Color strength was assessed as acceptable if the grade according to the following criteria was A, B, or C for both fabrics (i.e., not D for any of the two fabrics).

$$C^* = \{(a^*)^2 + (b^*)^2\}^{1/2} \quad \text{(Equation 1)}$$

A: C*max is 60 or more.
B: C*max is 55 or more and less than 60.
C: C*max is 50 or more and less than 55.
D: C*max is less than 50.

5.4. Hue Variability Evaluation

For the evaluation samples obtained in "5.3. Color Strength Evaluation," the L*, a*, and b* values of the image were measured in the same way, using a spectrodensitometer (trade name, "Spectrolino"; X-Rite) and under the following conditions: light source, D65; status, DIN_NB; angle of view, 2 degrees; filter, UV. The difference in hue (ΔE*) between fabric 1 (100% cotton; grammage, 130 g/m²) and fabric 2 (100% silk, grammage, 90 g/m²) was calculated, and hue variability was assessed against the following criteria.

$$\Delta E^* = \{(\Delta L^*)^2 + (\Delta a^*)^2 + (\Delta b^*)^2\}^{1/2} \quad \text{(Equation 2)}$$

$$\Delta L^* = L^*_1 - L^*_2 \quad \text{(Equation 3)}$$

$$\Delta a^* = a^*_1 - a^*_2 \quad \text{(Equation 4)}$$

$$\Delta b^* = b^*_1 - b^*_2 \quad \text{(Equation 5)}$$

In these equations, $L^*_1$, $a^*_1$, and $b^*_1$ represent the L*, a*, and b* values, respectively, of the area where C*max was achieved (C*max area) of fabric 1 (100% cotton; grammage, 130 g/m²), and $L^*_2$, $a^*_2$, and $b^*_2$ represent the L*, a*, and b* values, respectively, of the C*max area of fabric 2 (100% silk; grammage, 90 g/m²). Hue variability was assessed as acceptable if the grade according to the following criteria was A, B, or C (i.e., not D).

A: ΔE* is less than 3.0.
B: ΔE* is 3.0 or more and less than 5.0.
C: ΔE* is 5.0 or more and less than 8.0.
D: ΔE* is 8.0 or more.

5.5. Light Fastness Evaluation

Using a xenon weather meter (trade name, "XL-75s"; Suga Test Instruments), the C*max area of the evaluation samples of fabric 1 (100% cotton; grammage, 130 g/m²) and fabric 2 (100% silk; grammage, 90 g/m²) was exposed to light of 75000 lux at 23° C. and 50% RH for 10 days. The difference in hue (ΔE*) between baseline and day 10 was calculated as in "5.4. Hue Variability Evaluation," and light fastness was graded against the criteria below. Light fastness was assessed as acceptable if the grade according to the criteria below was A, B, or C for both fabrics (i.e., not D for any of the two fabrics).

A: ΔE* is less than 10.
B: ΔE* is 10 or more and less than 12.5.
C: ΔE* is 12.5 or more and less than 15.
D: ΔE* is 15 or more.

5.6. Evaluation of Nozzle-Plate Water Repellency 5.6.1. Preparation of Nozzle Plates Co-deposition plating was formed on the surface of some nozzle plates and plasma-polymerized and fluoropolymer coatings on the surface of some others, giving two kinds of nozzle plates with a liquid-repellent coating on their surface.

The co-deposition plating was formed by dipping SUS316 nozzle plates into plating solution (nickel sulfate, 240 g/L; nickel chloride, 45 g/mL; boric acid, 35 g/mL; PTFE, 50 g/L) and gently stirring the solution under the following conditions: pH, 4.0 to 4.5; plating temperature, 60° C.; cathode current density, 3 A/dm².

The plasma-polymerized and fluoropolymer coatings were formed by covering SUS316 nozzle plates with a plasma-polymerized coating of dimethylpolysiloxane (SH200, Dow Corning Toray Silicone) and a monolayer of heptatriacontafluoroicosyltrimethoxysilane (Optool DSX™, Daikin Industries). The following is a more detailed description of the formation of these coatings.

In a plasma polymerization chamber, uncoated nozzle plates were maintained at 40° C. Argon gas was supplied into the chamber and its pressure was kept at 7 Pa. A radio-frequency power of 100 W was applied to generate argon plasma. Dimethylpolysiloxane was introduced into the chamber, so that it polymerized into a plasma-polymerized coating on the surface of the nozzle plates. The resulting plasma-polymerized coating was annealed in a nitrogen atmosphere at 200° C., and its surface was exposed to argon plasma for 1 minute. The plasma-polymerized coating was then exposed to the air, so that hydrogen atoms bound with terminal oxygen atoms on the surface of the coating, forming OH groups. Heptatriacontafluoroicosyltrimethoxysilane had been mixed into solvent (trade name, HFE-7200; Sumitomo 3M) to give a solution having a concentration of, for example, 0.1 wt % beforehand. The nozzle plates with a plasma-polymerized coating thereon were heated to 300° C. and dipped into this solution. In this way, nozzle plates with plasma-polymerized and fluoropolymer coatings thereon were obtained.

5.6.2. Water-Repellency Study

Twenty grams each of the ink compositions of Examples 3, 6, and 15 and Comparative Example 1 were put into separate Teflon® containers. The containers were stored sealed with a lid at 60° C., with two nozzle plates immersed in the ink composition, one with co-deposition plating and the other with plasma-polymerized and fluoropolymer coatings. The water-repellent coating on the surface of each nozzle plate was visually inspected at days 1, 3, 7, and 14, and the length of time until the ink composition ran off, or "the time to repel," was compared between baseline and after storage. The results are presented in Table 4, where the grades represent the resistance of the coatings to corrosion by each ink composition as determined against the criteria below. It should be noted that when a coating loses its liquid repellency, its time to repel extends because of increasing difficulty for the ink composition to run off.

A: No change from baseline (before storage). The appearance remains the same, and the time to repel does not extend.

B: The appearance of the liquid-repellent coating remains the same, but the time to repel extends.

C: The appearance of the liquid-repellent coating changes, and the time to repel extends.

D: No liquid-repellent effect. The liquid-repellent coating detaches, exposing the SUS plate.

TABLE 4

| Liquid-repellent coating(s) | Ink composition | Period of immersion (60° C.) | | | |
|---|---|---|---|---|---|
| | | 1 day | 3 days | 7 days | 14 days |
| Co-deposition plating on the nozzle plate | Example 3 | A | B | C | D |
| | Example 6 | A | B | C | D |
| | Example 15 | B | C | D | D |
| | Comparative Example 1 | C | D | D | D |
| Plasma-polymerized and fluoropolymer coatings on the nozzle plate | Example 3 | A | A | A | A |
| | Example 6 | A | A | A | A |
| | Example 15 | A | A | A | A |
| | Comparative Example 1 | A | A | C | D |

5.7. Color Gamut Evaluation 5.7.1. Ink Sets

Ink compositions were prepared by mixing the ingredients (materials) as set forth in Table 5, thoroughly stirring the mixture to homogeneity, and filtering the resulting blend through a membrane filter (pore size, 1 μm). The values in Table 5 are in % by mass, with the total being 100% by mass.

which all of the CIE L*, a*, and b* values are 1 corresponds to a gamut of 1. The gamut of each ink set was graded against the criteria below, with that of ink set 3 assumed to be 100%.

A: The gamut is more than 110%.

B: The gamut is more than 100% and 110% or less.

C: The gamut is 100% or less.

TABLE 6

| | | Ink set 1 | Ink set 2 | Ink set 3 |
|---|---|---|---|---|
| Inks | Y | Ink Y1, Table 5 | Ink Y2, Table 5 | Ink Y1, Table 5 |
| | M | Ink 3, Table 1 | Ink 3, Table 1 | Ink M1, Table 5 |
| | C | Ink C1, Table 5 | Ink C2, Table 5 | Ink C1, Table 5 |
| | K | Ink K1, Table 5 | Ink K1, Table 5 | Ink K1, Table 5 |
| Color gamut | | A | A | Assumed to be 100% |

5.8. Evaluation Results

According to the evaluation results, the ink compositions of Examples, containing RR24:1, RR141, and/or RR245, all included in the structure of formula (I), as first dye(s) and RV1 and/or RV33, both included in the structure of formula (II), as second dye(s), were stable over time in terms of pH and gave prints high color strength and high hue stability (light fastness). These ink compositions also had a wide

TABLE 5

| | | | Ink | | | | | |
|---|---|---|---|---|---|---|---|---|
| | | | Ink Y1 | Ink Y2 | Ink M1 | Ink C1 | Ink C2 | Ink K1 |
| Formula of the ink composition | Dye (not first or second dyes) | RY95 | 7 | — | — | — | — | — |
| | | RY2 | — | 7 | — | — | — | — |
| | | RR24:1 | — | — | 11 | — | — | — |
| | | RB72 | — | — | — | 7 | — | — |
| | | RB15:1 | — | — | — | — | 7 | — |
| | | RBk39 | — | — | — | — | — | 10 |
| | Water-soluble solvents | 1,2-Hexanediol (223° C.) | 3 | 3 | 3 | 3 | 3 | 3 |
| | | Propylene glycol (188° C.) | 10 | 10 | 10 | 10 | 10 | 10 |
| | | 2-Pyrrolidone (245° C.) | 10 | 10 | 10 | 10 | 10 | 10 |
| | | Glycerol (290° C.) | — | — | — | — | — | — |
| | Water-attracting agent | Urea | 3 | 3 | 3 | 3 | 3 | 3 |
| | Surfactant | Olfine PD002W | 0.2 | 0.2 | 0.2 | 0.2 | 0.2 | 0.2 |
| | pH-adjusting agent | Triethanolamine | 0.3 | 0.3 | 0.3 | 0.3 | 0.3 | 0.3 |
| | | Tripropanolamine | — | — | — | — | — | — |
| | | Adipic acid | 0.05 | 0.05 | 0.05 | 0.05 | 0.05 | 0.05 |
| | Water | Ion-exchanged water | Balance | Balance | Balance | Balance | Balance | Balance |
| | | Total | 100 | 100 | 100 | 100 | 100 | 100 |

In Table 5, "RY," "RR," "RB," and "RBk" stand for "C.I. Reactive Yellow," "C.I. Reactive Red," "C.I. Reactive Blue," and "C.I. Reactive Black," respectively. Ink sets 1 to 3, in Table 6, were prepared as combinations of ink 3, detailed in Table 1, with the ink compositions in Table 5.

5.7.2. Calculation of Color Gamut

For each of ink sets 1 to 3, in Table 6, the color gamut of in textile printing was calculated. The ink set was loaded into PX-G930 printer (Seiko Epson Corporation), a lookup table covering the RGB range of (0, 0, 0) to (255, 255, 255) was printed on fabric 1 (100% cotton; grammage, 130 g/m²), and the resulting evaluation sample was analyzed under the same conditions as in "Hue Variability Evaluation." From the obtained L*, a*, and b* values, the color gamut of the ink composition was calculated assuming that a color space in range of compatibility with fabrics. With these ink compositions, the hue was similar between printing on cotton and that on silk.

The ink composition of Comparative Example 1, in which RR31, not included in the structure of formula (I) or that of (II), was the only dye, was inferior in storage stability, color strength, and light fastness. The ink composition of Comparative Example 3, in which AR138 and AV97, both not included in the structure of formula (I) or that of (II), were the only dyes, was inferior in color strength, hue variability, and light fastness. Comparative Example 2, in which a large amount of RR31 was used, was inferior in all evaluations excluding color strength. The ink compositions of Comparative Examples 4 and 5, in which only a first or second dye was used, were inferior in hue variability (range of compatibility with fabrics).

Examples 10 to 12 were slightly inferior in hue variability and light fastness. In these examples, the second dye was RV33 instead of RV1 and used in a relatively large amount, indicating that RV1 is more resistant to light than RV33. Given this, there appears to be a compatibility issue between first and second dyes; some combinations work well, but some others do not. The ink compositions of Examples 18 to 21, containing multiple first dyes and multiple second dyes, also achieved good results.

As can be seen from Table 4, nozzle plates with co-deposition plating thereon underwent a change in appearance in 3 days when immersed in ink 15, of Example 15. With inks 3 and 6, of Examples 3 and 6, respectively, the change in appearance was observed in 7 and 14 days, respectively. This suggests that for a nozzle plate covered with plating formed by co-deposition, the number of days until its surface appearance changes, and therefore the shelf life of the nozzle plate, vary according to the ink used. The results also indicate that for a nozzle plate covered with plating formed by co-deposition, the number of days until its surface appearance changes increases with a rise in the pH of the ink used, and that the co-deposition plating is degraded in linear correlation with the pH of the ink used.

In contrast, nozzle plates with plasma-polymerized and fluoropolymer coatings thereon exhibited superb corrosion resistance. These nozzle plates remained unchanged in appearance for 14 days with all of the inks according to an aspect of the invention.

The invention is not limited to the above embodiments and many variations are possible. For example, the invention embraces configurations substantially identical to those described in the embodiments (e.g., configurations identical in function, methodology, and results to or having the same goal and offering the same advantages as the described ones). The invention also includes configurations created by changing any nonessential part of those described in the above embodiments.

Furthermore, the invention encompasses configurations identical in operation and effect to or capable of fulfilling the same purposes as those described in the above embodiments. Configurations obtained by adding any known technology to those described in the embodiments are also part of the invention.

The entire disclosures of Japanese Patent Application Nos. 2016-126472, filed Jun. 27, 2016 and 2017-106597, filed May 30, 2017 are expressly incorporated by reference herein.

What is claimed is:

1. An ink set comprising:
a first ink composition;
a yellow ink composition containing C.I. Reactive Yellow 95 or C.I. Reactive Yellow 2;
a cyan ink composition containing C.I. Reactive Blue 72 or C.I. Reactive Blue 15:1; and
a black ink composition containing C.I. Reactive Black 39, wherein the first ink composition includes:
at least one first dye represented by formula (I),

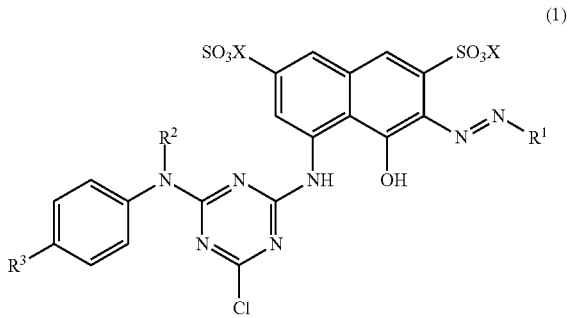

where $R^1$ denotes

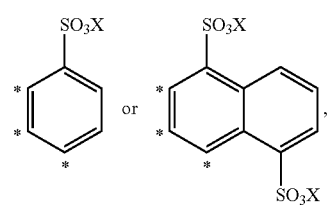

$R^2$ denotes H, $CH_3$ or $C_2H_5$, and
$R^3$ denotes H or

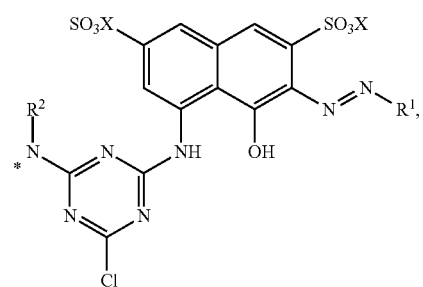

where X denotes H, Li, Na, or K,
with possible binding sites labeled with an asterisk; and
at least one second dye represented by formula (II),

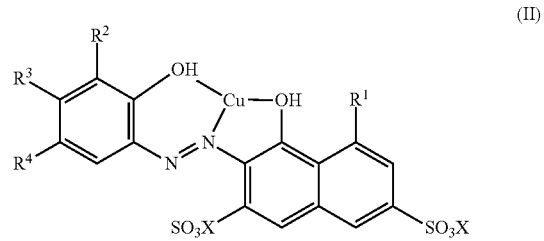

where R¹ denotes SO₃X or

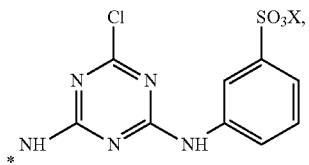

R², R³, and R⁴ each independently denote H, SO₃X, a halogen, or

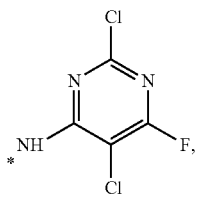

and
X denotes H, Li, Na, or K,
with possible binding sites labeled with an asterisk.

2. The ink set according to claim 1, wherein the first ink composition has a pH of 6.0 or more and 8.5 or less.

3. The ink set according to claim 1, wherein the first ink composition further comprises a pH-adjusting agent.

4. The ink set according to claim 1, wherein the first ink composition contains no or up to 5% by mass, of a total amount of the first ink composition, polyhydric alcohols with boiling points higher than 260° C.

5. The ink set according to claim 1, wherein in the first ink composition:
the at least one first dye is selected from C.I. Reactive Red 141, C.I. Reactive Red 24:1, and C.I. Reactive Red 245; and
the at least one second dye is selected from C.I. Reactive Violet 1 and C.I. Reactive Violet 33.

6. An ink set comprising:
the first ink composition according to claim 2;
a yellow ink composition containing C.I. Reactive Yellow 95 or C.I. Reactive Yellow 2;
a cyan ink composition containing C.I. Reactive Blue 72 or C.I. Reactive Blue 15:1; and
a black ink composition containing C.I. Reactive Black 39.

7. An ink set comprising:
the first ink composition according to claim 3;
a yellow ink composition containing C.I. Reactive Yellow 95 or C.I. Reactive Yellow 2;
a cyan ink composition containing C.I. Reactive Blue 72 or C.I. Reactive Blue 15:1; and
a black ink composition containing C.I. Reactive Black 39.

8. An ink set comprising:
the first ink composition according to claim 4;
a yellow ink composition containing C.I. Reactive Yellow 95 or C.I. Reactive Yellow 2;
a cyan ink composition containing C.I. Reactive Blue 72 or C.I. Reactive Blue 15:1; and
a black ink composition containing C.I. Reactive Black 39.

9. An ink set comprising:
the first ink composition according to claim 5;
a yellow ink composition containing C.I. Reactive Yellow 95 or C.I. Reactive Yellow 2;
a cyan ink composition containing C.I. Reactive Blue 72 or C.I. Reactive Blue 15:1; and
a black ink composition containing C.I. Reactive Black 39.

10. A recording method comprising ejecting at least one ink composition from the ink set according to claim 1 from an ink jet recording head that has a nozzle plate containing fluorine in at least part of a surface thereof and having siloxane bonds less than 1 μm beneath the surface.

11. A recording method comprising ejecting the first ink composition according to claim 2 from an ink jet recording head that has a nozzle plate containing fluorine in at least part of a surface thereof and having siloxane bonds less than 1 μm beneath the surface.

12. A recording method comprising ejecting the first ink composition according to claim 3 from an ink jet recording head that has a nozzle plate containing fluorine in at least part of a surface thereof and having siloxane bonds less than 1 μm beneath the surface.

13. A recording method comprising ejecting the first ink composition according to claim 4 from an ink jet recording head that has a nozzle plate containing fluorine in at least part of a surface thereof and having siloxane bonds less than 1 μm beneath the surface.

14. A recording method comprising ejecting the first ink composition according to claim 5 from an ink jet recording head that has a nozzle plate containing fluorine in at least part of a surface thereof and having siloxane bonds less than 1 μm beneath the surface.

15. An ink composition for ink jet textile printing, the ink composition comprising:
at least one first dye represented by formula (I),

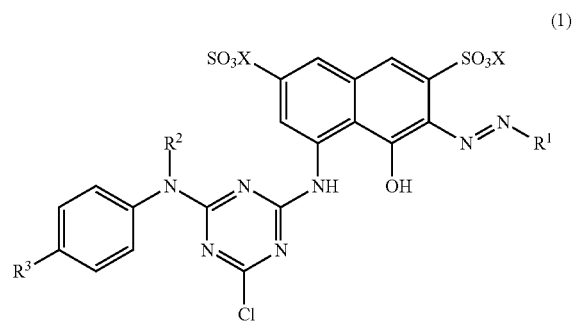

where R¹ denotes

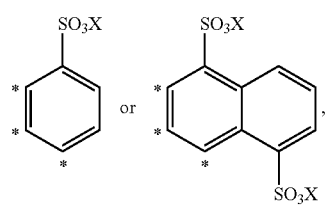

$R^2$ denotes $CH_3$ or $C_2H_5$, and
$R^3$ denotes H, or

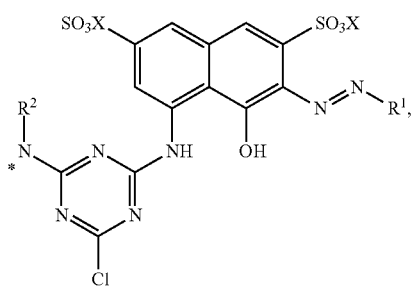

where X denotes H, Li, Na, or K,
with possible binding sites labeled with an asterisk; and
at least one second dye represented by formula (II), (II)

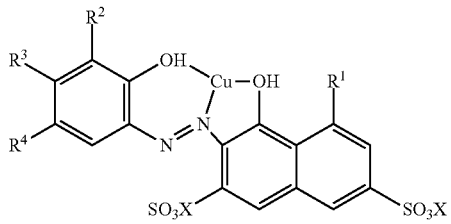

where $R^1$ denotes $SO_3X$ or

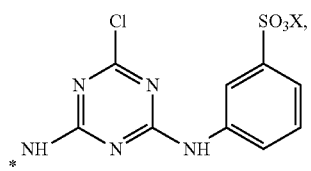

$R^2$, $R^3$, and $R^4$ each independently denote H, $SO_3X$, a halogen, or

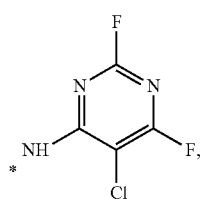

and
X denotes H, Li, Na, or K,
with possible binding sites labeled with an asterisk.

16. An ink composition for ink jet textile printing, the ink composition comprising:
at least one first dye represented by formula (I),

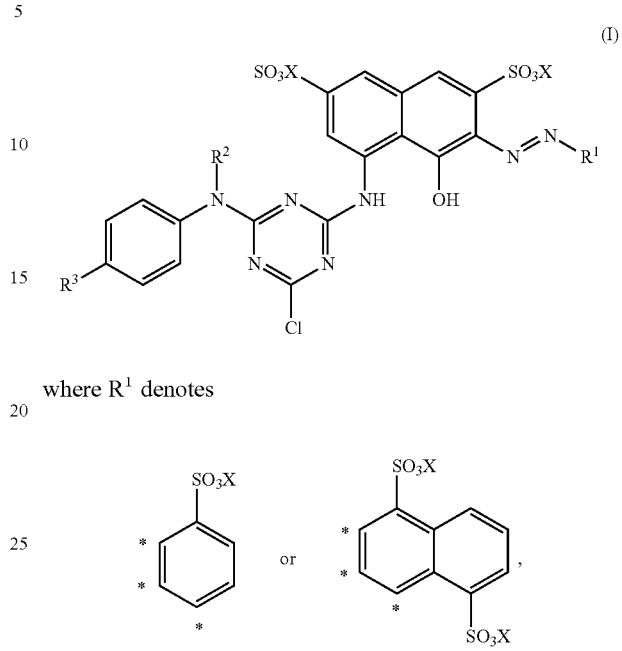

where $R^1$ denotes

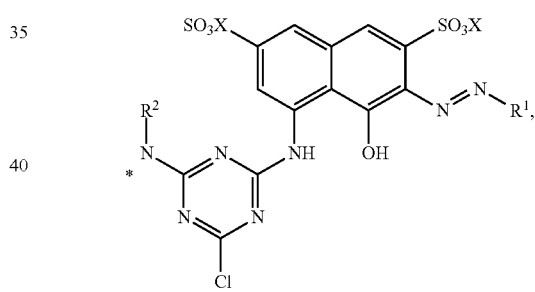

$R^2$ denotes H, $CH_3$, or $C_2H_5$, and
$R^3$ denotes H or

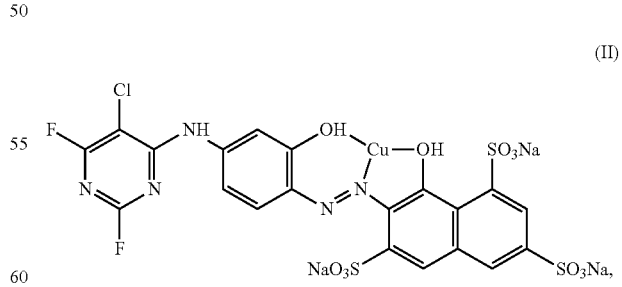

where X denotes H, Li, Na, or K,
with possible binding sites labeled with an asterisk; and
at least one second dye represented by formula (II), (II)

with possible binding sites labeled with an asterisk.

* * * * *